(12) United States Patent
Itomi

(10) Patent No.: US 7,112,973 B2
(45) Date of Patent: Sep. 26, 2006

(54) OIL CONDITION SENSOR

(75) Inventor: Shoji Itomi, Kuwana (JP)

(73) Assignee: NTN Corporation, Osaka (JP)

( * ) Notice: Subject to any disclaimer, the term of this patent is extended or adjusted under 35 U.S.C. 154(b) by 0 days.

(21) Appl. No.: 11/260,289

(22) Filed: Oct. 28, 2005

(65) Prior Publication Data

US 2006/0125487 A1    Jun. 15, 2006

(30) Foreign Application Priority Data

Dec. 13, 2004    (JP) .............................. 2004-360271

(51) Int. Cl.
  *G01R 27/08*    (2006.01)
  *G01N 33/20*    (2006.01)
(52) U.S. Cl. ...................... 324/698; 324/724; 73/61.42
(58) Field of Classification Search ................ 324/553, 324/698, 693, 691, 649, 600, 439, 446, 705, 324/722, 696, 724, 204, 219, 71.1, 228; 73/53.05, 73/53.06, 53.07, 61.42, 61.71
See application file for complete search history.

(56) References Cited

U.S. PATENT DOCUMENTS

| 4,323,843 A | * | 4/1982 | Batham ...................... 324/204 |
| 5,457,396 A | * | 10/1995 | Mori et al. .................. 324/724 |
| 5,614,830 A | * | 3/1997 | Dickert et al. ............... 324/553 |
| 6,377,052 B1 | * | 4/2002 | McGinnis et al. ........... 324/446 |
| 6,556,026 B1 | * | 4/2003 | Ogimoto et al. ............. 324/698 |
| 6,803,775 B1 | * | 10/2004 | Sanchez et al. ............. 324/698 |

FOREIGN PATENT DOCUMENTS

JP    2002-286697    10/2002

* cited by examiner

*Primary Examiner*—Anjan Deb
*Assistant Examiner*—Hoai-An D. Nguyen
(74) *Attorney, Agent, or Firm*—Wenderoth, Lind & Ponack, L.L.P.

(57) ABSTRACT

An oil condition sensor includes rod-shaped electrodes and an opposed cup-shaped electrode. The rod-shaped electrodes are connected to a first power supply through first fixed resistors having a predetermined threshold. The voltage from the first power supply is applied through the respective rod-shaped electrodes to first inputs of respective operational amplifiers. The sensor further includes a second power supply which produces a voltage applied to second inputs of the respective operational amplifiers. Each operational amplifier produces a predetermined voltage if the voltage applied to the first input falls below the voltage applied to the second input. The output of each operational amplifier is connected to the second input through a second fixed resistor. There is a hysteresis relation between the input and output of the amplifiers, so that once an operational amplifier produces voltage, even if voltage from the corresponding conductor falls thereafter, the operational amplifier continuously produces voltage.

3 Claims, 4 Drawing Sheets

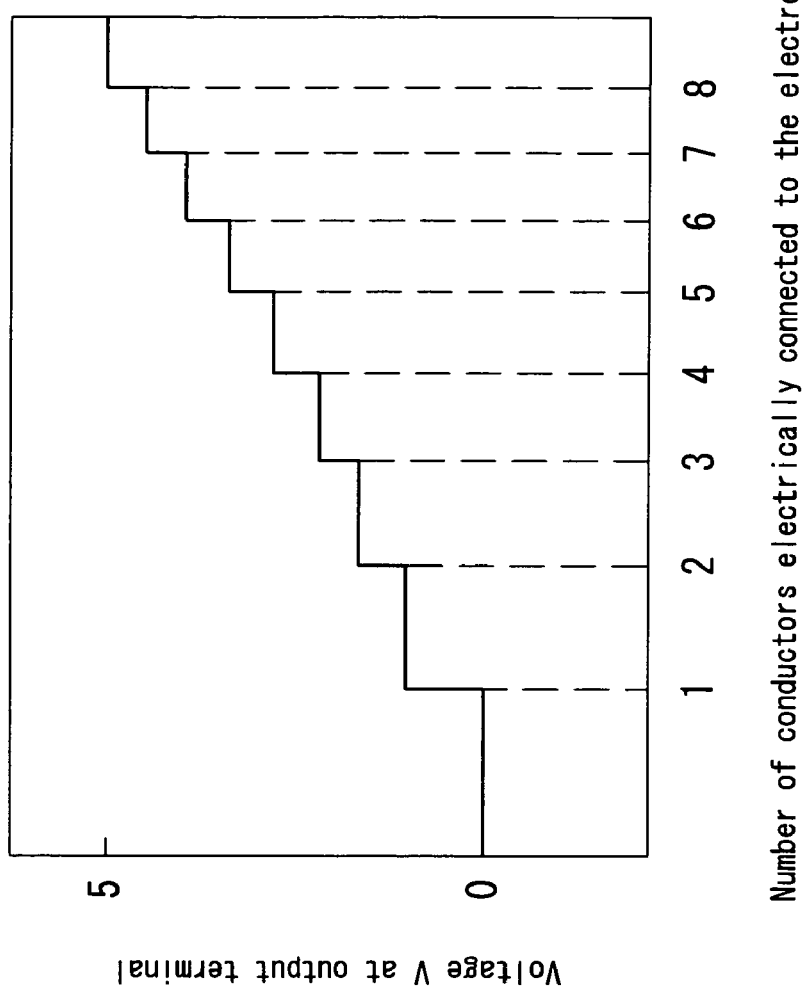

OIL CONDITION SENSOR

BACKGROUND OF THE INVENTION

The present invention relates to an oil condition sensor used to check the degree of contamination of automotive transmission oil or engine oil.

Such an oil condition sensor is mounted in an oil container for automotive transmission oil or engine oil and is used to check the degree of contamination of the oil with iron powder or other metallic powder that are produced when automotive parts are abraded against each other. A typical such sensor is disclosed in JP patent publication 2002-286697A (see especially its FIGS. 1–4). It includes a rod adapted to be immersed in oil. The rod carries magnets at its tip. A pair of electrodes are provided around the magnets, axially spaced from and opposed to each other. The sensor produces a signal corresponding to the resistance in the oil between the electrodes, which in turn corresponds to the amount of metallic powder in the oil. At least one of the pair of electrodes comprises a resistor. By detecting the resistance between the electrodes which changes with the area of the end face of the resistor covered by iron powder that is magnetically attracted toward the outer surface of the magnets and stuck on the end face of the resistor, it is possible to detect the amount of iron powder in the oil.

In this publication, it is necessary to use a resistor as one of the pair of electrodes or on the outer periphery of an insulating cover provided on the inner periphery of the electrodes. Such a resistor tends to be internally stressed when the load and/or temperature changes. Such internal stresses in turn change the carbon sequence, thereby causing fluctuations in the specific resistance of the resistor. Because the specific resistance thus easily fluctuates, it is impossible to stably and reliably detect the resistance between the electrodes, so that no accurate determination of the degree of contamination of oil is possible.

In order to a solve this problem, the inventor of the present invention proposed an oil condition sensor in (JP patent application 2004-91029) which uses no resistors, of which the specific resistance tends to fluctuate according to the load applied and the temperature, and thus can stably check the degree of contamination of oil. This oil condition sensor includes a pair of electrodes with one of the electrodes comprising a plurality of conductors each arranged so as to oppose the other electrode. By counting the number of conductors that are electrically connected to the other electrode through metallic powder in the oil, it is possible to stably detect the amount of metallic powder in the oil. In order to count the number of conductors that are electrically connected to the other electrode, the conductors are connected to a power supply through separate fixed resistors or other members that react to electricity.

The inventor of the present invention also proposed in JP patent application 2004-148984 an oil condition sensor including conductors similar to those disclosed in JP patent application 2004-91029 which are connected to a power supply through separate resistors having different resistances from each other. By counting the number of conductors that are electrically connected to the other opposed electrode, it is possible to detect the amount of metallic powder in the oil. The resistances of the resistors are determined such that the number of conductors that are electrically connected to the other opposed electrode will be in a linear relationship with the sensor output.

In either of the oil condition sensors, since metallic powder stuck on the electrodes is in oil, of which the temperature fluctuates, when the oil temperature rises and its viscosity decreases, metallic powder particles tend to more closely contact each other. The electrical resistance between the electrodes thus decreases. Conversely, when the oil temperature falls and its viscosity increases, metallic powder particles tend to less closely contact each other, thus increasing the electrical resistance between the electrodes.

Thus, even if the amount of metallic powder stuck on the electrodes is unchanged, the number of conductors that are electrically connected to the opposed electrode or the sensor output may change if the oil temperature changes. In particular, if the oil temperature falls, even if the amount of metallic powder stuck on the electrodes is unchanged or increases, the number of conductors electrically connected to the opposed electrode or the sensor output may fall.

An object of the present invention is to provide an oil condition sensor which can stably check the degree of contamination of oil even if the oil temperature changes.

SUMMARY OF THE INVENTION

According to the present invention, there is provided an oil condition sensor comprising a rod having a tip configured to be immersed in oil, a magnet provided around the tip of the rod, first and second electrodes mounted around the magnet, the first electrode comprising a plurality of conductors axially opposing the second electrode, and an arrangement for comparing the electrical resistance between each of the conductors and the second electrode with a threshold, and producing a predetermined voltage if the electrical resistance between any of the conductors and the second electrode is smaller than the threshold, thereby detecting the amount of metallic powder in the oil.

By producing a predetermined voltage if the electrical resistance between any of the conductors and the second electrode is smaller than the threshold, it is possible to stably check the degree of contamination of oil with metallic powder even if the oil temperature changes.

Preferably, the abovementioned arrangement comprises an electric circuit.

The electric circuit preferably comprises a first power supply electrically connected to the respective conductors through first fixed resistors having an electrical resistance equal to the threshold, operational amplifiers each corresponding to one of the conductors and having a first input connected to the one of the conductors, a second input and an output, the first power supply producing a voltage which is applied to the first inputs of the operational amplifiers through the first fixed resistors and the conductors, and a second power supply for applying a predetermined voltage to the second inputs of the operational amplifiers, the output of each of the operational amplifiers being electrically connected to the second input through a second fixed resistor having a predetermined electrical resistance, each of the operational amplifiers being configured to produce a predetermined voltage from the output if the voltage applied to the first input is lower than the voltage applied to the second input. With this arrangement, there is a hysteresis relation between the input and output of the operational amplifiers, so that even if the electrical resistance between the electrodes exceeds the threshold after it has fallen below the threshold due e.g. to an increase in the oil temperature, the operational amplifiers will keep producing a constant voltage.

BRIEF DESCRIPTION OF THE DRAWINGS

Other features and objects of the present invention will become apparent from the following description made with reference to the accompanying drawings, in which:

FIG. 4 is a graph showing the relationship between the voltage at the output terminal and the number of conductors that are electrically connected to the opposed electrode.

DETAILED DESCRIPTION OF THE PREFERRED EMBODIMENTS

Figure 1:
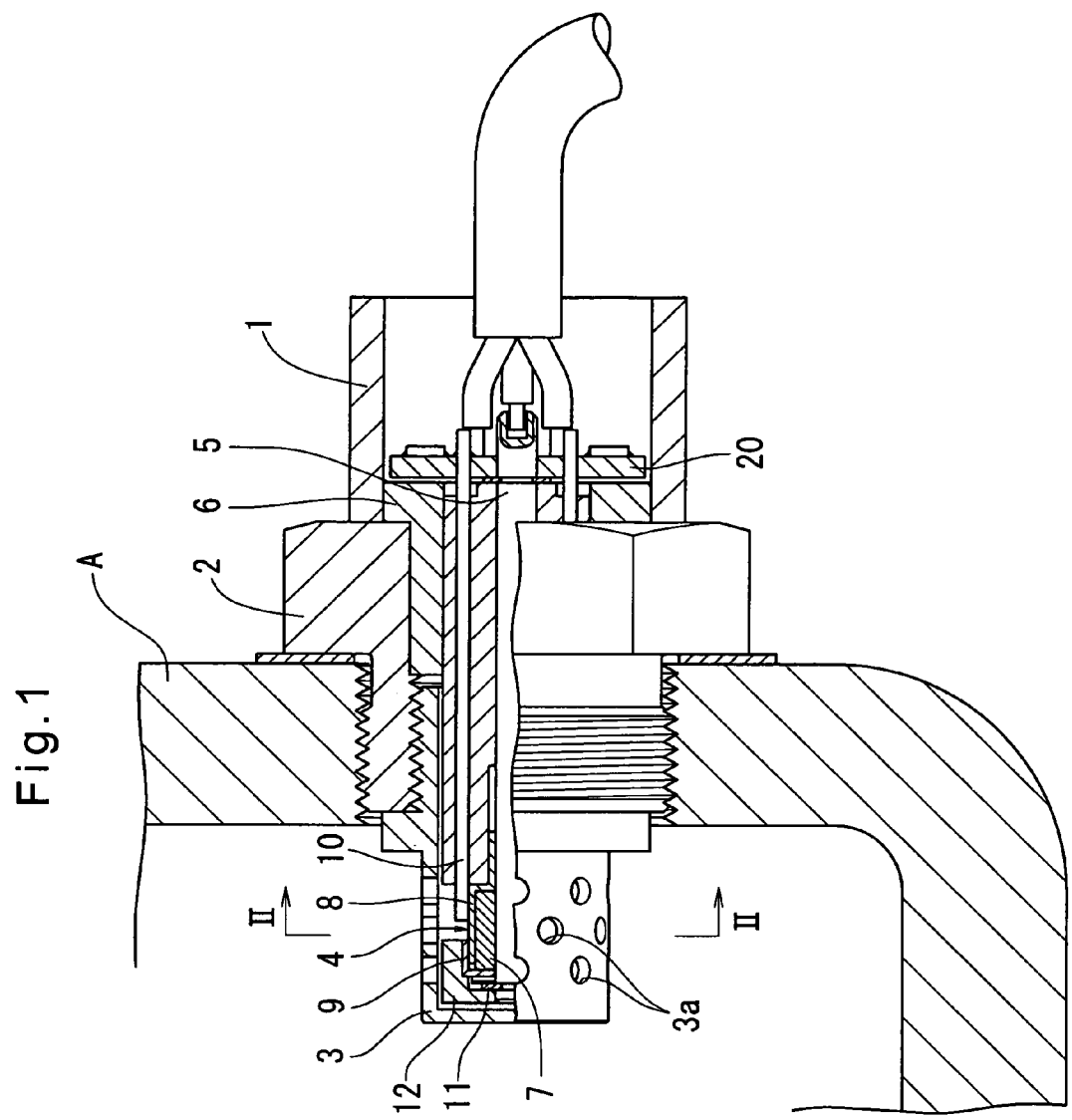
FIG. 1 is a partially vertically sectional view of an oil condition sensor embodying the present invention.
Figure 2:
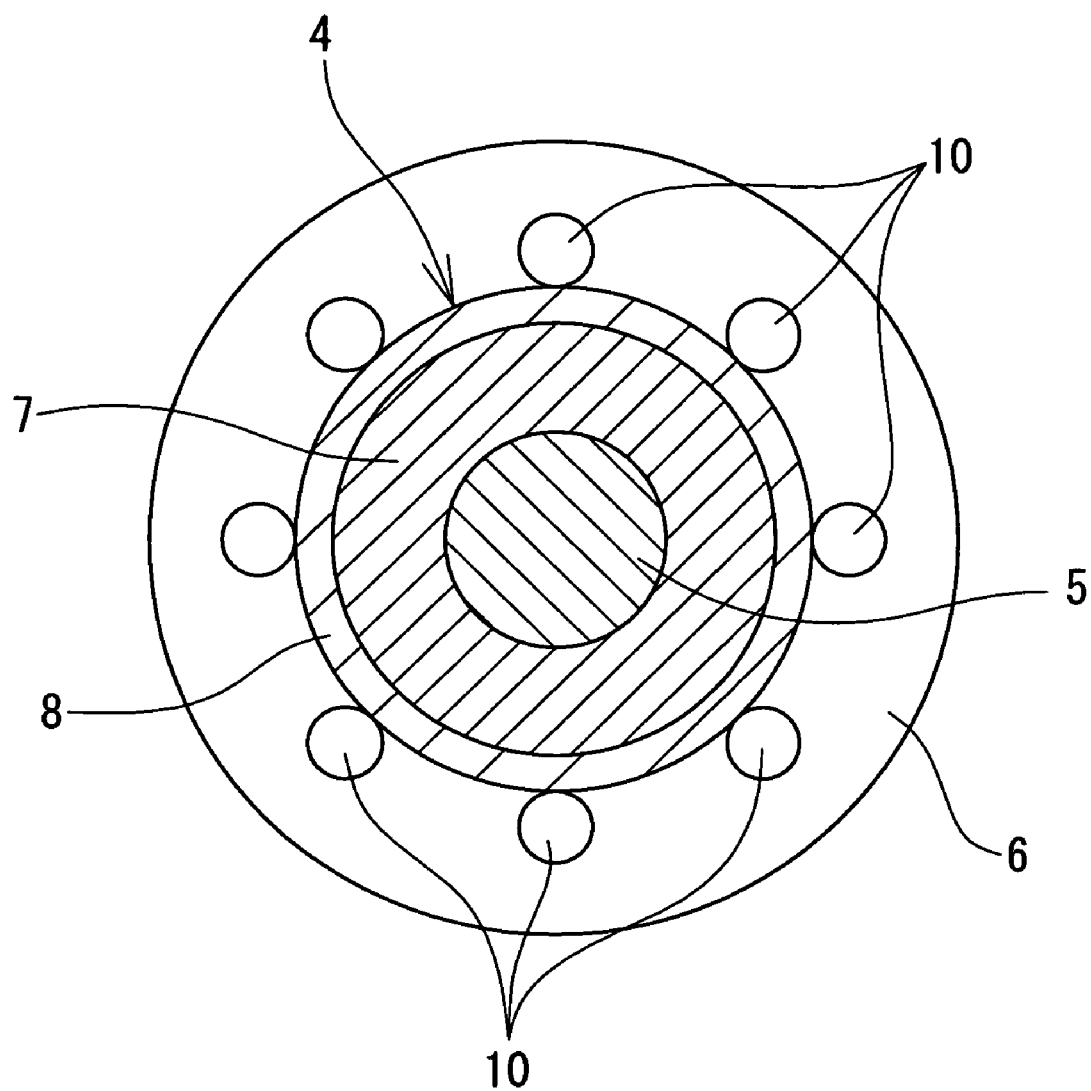
FIG. 2 is a sectional view taken along line II—II of FIG. 1.

An embodiment of the present invention is now described with reference to the drawings. The oil condition sensor of the embodiment is used to check the degree to which automotive transmission oil is contaminated with metallic powders, and includes, as shown in FIGS. 1 and 2, a nut 2 threaded into a lower portion of a side wall of an oil pan A for transmission oil, a casing 1 fixed to the nut 2 outside of the oil pan A, and a head cover 3 threaded into the nut 2 inside of the oil pan A so as to be immersed in the oil. A sensor head assembly 4 is mounted in the head cover 3. The head cover 3 is formed with a plurality of holes 3a through which oil in the oil pan A can flow into the head cover 3.

A rod 5 made of a conductive material extends through the casing 1 and is held in position so as to be coaxial with the casing 1 by a holder 6 received in the casing 1. A ring-shaped permanent magnet 7 is fitted around the tip of the rod 5 protruding from the holder 6 into the casing 1. A tubular insulating cover 8 is provided around the permanent magnet 7. A cup-shaped electrode 9 is fitted on and electrically connected to the rod 5 so as to surround the insulating cover 8. A plurality of (eight in the embodiment shown) rod-shaped conductors 10 extend through the holder 6 with their end portions protruding therefrom into the head cover 3 so as to axially oppose the rear end face (right-hand end in FIG. 1) of the electrode 9 around the rod 5. The sensor head assembly 4 comprises all of these elements. The electrodes 10 are connected to an electric circuit 20, which is to be described later.

The eight rod-shaped electrodes 10 are circumferentially spaced from each other at equal intervals around the rod 5. The cup-shaped electrode 9 is fixed to the tip of the rod 5 by means of a snap ring 11 so as not to come off the rod 5. With the exception of the end face opposing the rod-shaped electrodes 10, the exposed surface of the cup-shaped electrode 9 is covered by a shield member 12. The shield member 12 thus prevents metallic powder from adhering to the exposed surface of the electrode 9 other than the end face thereof even though the electrode 9 is magnetized by the permanent magnet 7.

Figure 3:
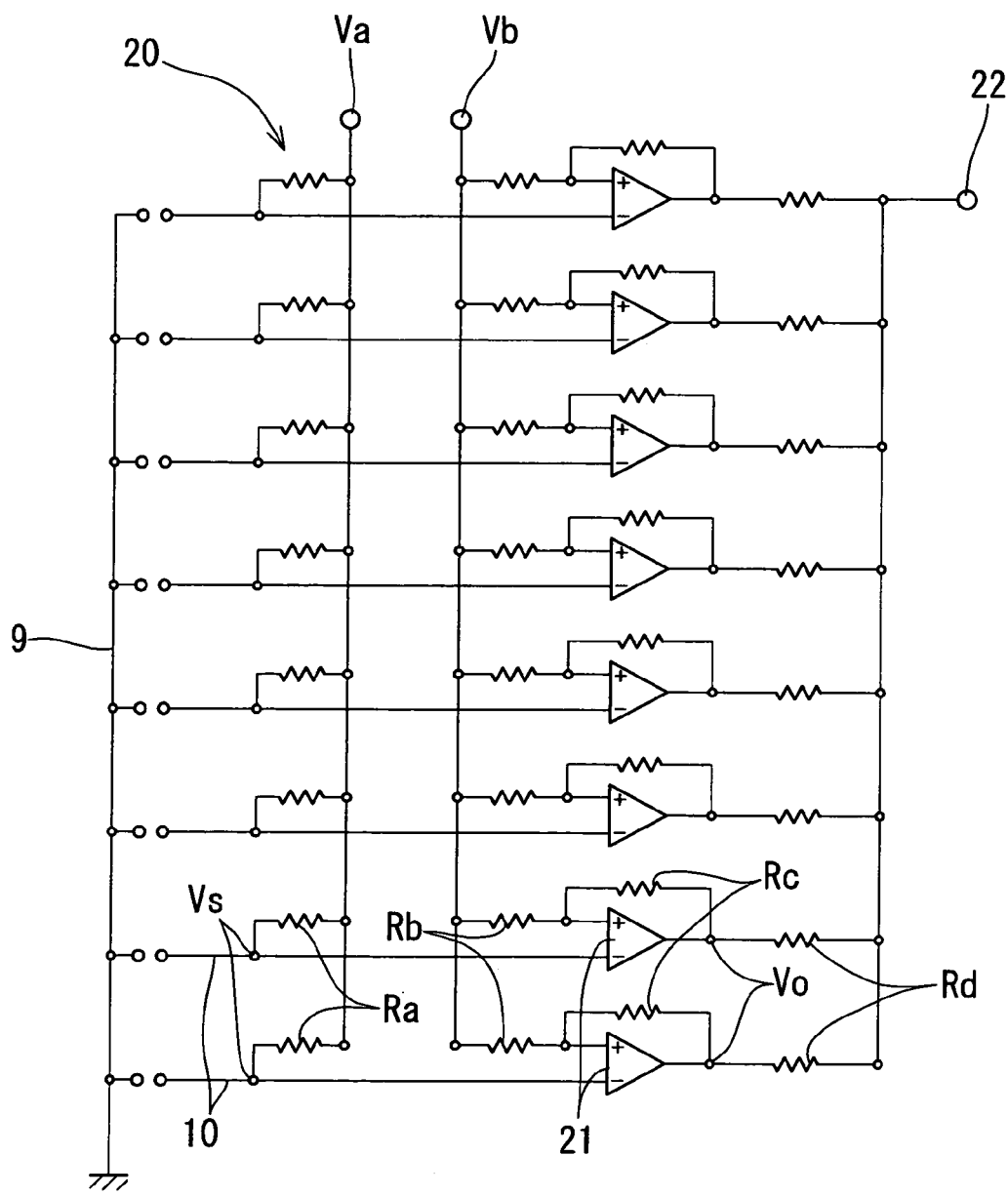
FIG. 3 is a circuit diagram of an electric circuit to which conductors of one of the electrodes are connected.

FIG. 3 shows the electric circuit 20, to which the rod-shaped electrodes 10 are connected. The cup-shaped electrode 9 is grounded. The eight rod-shaped electrodes 10 are connected to a power supply Va through fixed resistors Ra having a predetermined threshold and each connected to a negative terminal of one of a plurality of operational amplifiers 21. A predetermined reference voltage Vb is applied through fixed resistors Rb to positive terminals of the respective operational amplifiers 21. The outputs of the operational amplifiers 21 are connected through fixed resistors Rc to their respective positive terminals, to which the reference voltage Vb is applied, and are connected, in parallel to each other, to an output terminal 22 through fixed resistors Rd.

Description is now made of how each operational amplifier 21 produces a predetermined voltage if the electrical resistance between the corresponding electrode 10 and the electrode 9 falls below a predetermined threshold. In the embodiment, the power supply Va produces 5V, the reference voltage Vb is 2.5V, and the resistors have the following resistances: Ra=20 kΩ, Rb=10 kΩ, Rc=100 kΩ and Rd=10 kΩ. Each operational amplifier 21 is configured to produce an output voltage Vo of 5V if the voltage applied to its positive input terminal is higher than the voltage applied to its negative input terminal, and produces an output voltage Vo of 0V if the voltage applied to the positive input terminal is lower than the voltage applied to the negative input terminal. The output voltage Vo is multiplied by the factor of Rb/(Rb+Rc) and applied to the positive input terminal, to which the reference voltage Vb is also applied.

While the amount of metallic powder stuck on the electrodes 9 and 10 is small, so that the electrical resistance between the electrode 9 and any of the electrodes 10 is not less than the threshold of 20 kΩ, which is the resistance of the fixed resistor Ra, the voltage Vs applied to the negative input terminal from the corresponding electrode 10, which is connected to the power supply, will be 5V. On the other hand, to the positive input terminal of each amplifier 21, a voltage of 2.5V, which is the sum of the reference voltage Vb (2.5V) and the output voltage Vo (0V)×Rb/(Rb+Rc), is applied. Since the voltage applied to the positive input terminal is lower than the voltage applied to the negative input terminal, the operational amplifiers 21 will produce an output voltage of 0V.

If the amount of metallic powder stuck on the electrode 9 and one of the electrodes 10 increases to such an extent that the electrical resistance between the electrodes 9 and 10 is lower than the electrical resistance of 20 kΩ, which is the resistance of the resistor Ra, the voltage Vs from the electrode 10 will decrease to less than 2.5 V. Since the voltage applied to the positive input terminal remains 2.5V, which is the sum of the reference voltage Vb and the output voltage Vo×Rb/(Rb+Rc), the operational amplifier 21 produces a constant output voltage of 5V.

Once the output voltage Vo of the operational amplifier increases to 5V, about 0.5 V, which is the output voltage Vo multiplied by the factor of Rb/(Rb+Rc), is applied to the positive input terminal together with the reference voltage Vb of 2.5V, so that the voltage applied to the positive input terminal will increase from 2.5 V to about 3V. Thus, there is a hysteresis relation between the input and output of the operational amplifiers. That is, once the output voltage Vo increases to 5V, even if the electrical resistance between the electrodes 9 and 10 increases thereafter to a certain extent due e.g. to cooling of oil, so that the voltage Vs applied to the negative input terminal of the operational amplifier 21 from the electrode 10 increases slightly, the voltage Vs will be still lower than the voltage applied to the positive input terminal, which has been increased from 2.5V to about 3V. The operational amplifier 21 will thus not produce 0V.

FIG. 4 shows the relationship between the number n of operational amplifiers 21 that are producing a constant voltage of 5V and the voltage V detected at the output terminal 22. As shown, when all the amplifiers 21 are producing 0V, the voltage V will be also 0V. When only one of the eight operational amplifiers 21 is producing 5V, the voltage V at the output terminal 22 will be 5/8V. Thus, when n of the eight amplifiers 21 are producing 5V, the voltage V at the output terminal 22 will be 5n/8V, and when all of the amplifiers 21 are producing 5V, the voltage at the output terminal will be a maximum of 5V.

In the embodiment, eight rod-shaped electrodes 10 are used. But the number of electrodes 10 is not limited to eight. Also, the electrode 9 is not limited to a cup-shaped one, and the electrodes 10 are not limited to rod-shaped ones. The single electrode 9 may be replaced with a plurality of electrodes, too.

Instead of configuring the operational amplifiers such that there is a hysteresis relation between the input and output of the amplifiers as in the embodiment, the amplifiers according to the present invention may be configured such that their outputs are held and irreversible.

What is claimed is:

1. An oil condition sensor comprising a rod having a tip configured to be immersed in oil, a magnet provided around said tip of said rod, first and second electrodes mounted around said magnet, said first electrode comprising a plurality of conductors axially opposing said second electrode, and an arrangement for comparing the electrical resistance between each of said conductors and said second electrode with a threshold, and producing a predetermined voltage if the electrical resistance between any of said conductors and said second electrode is smaller than said threshold, thereby detecting the amount of metallic powder in the oil.

2. The oil condition sensor of claim 1 wherein said arrangement comprises an electric circuit.

3. The oil condition sensor of claim 2 wherein said electric circuit comprises a first power supply electrically connected to said respective conductors through first fixed resistors having an electrical resistance equal to said threshold, operational amplifiers each corresponding to one of said conductors and having a first input connected to said one of said conductors, a second input and an output, said first power supply producing a voltage which is applied to said first inputs of said operational amplifiers through said first fixed resistors and said conductors, and a second power supply for applying a predetermined voltage to said second inputs of said operational amplifiers, said output of each of said operational amplifiers being electrically connected to said second input through a second fixed resistor having a predetermined electrical resistance, each of said operational amplifiers being configured to produce a predetermined voltage from said output if the voltage applied to said first input is lower than the voltage applied to said second input.

* * * * *